(12) United States Patent
Deck et al.

(10) Patent No.: US 10,973,756 B2
(45) Date of Patent: Apr. 13, 2021

(54) SAND REMOVER FOR SKIN AND HAIR

(71) Applicants: Marla Christianne Deck, La Mesa, CA (US); David Aaron Deck, La Mesa, CA (US)

(72) Inventors: Marla Christianne Deck, La Mesa, CA (US); David Aaron Deck, La Mesa, CA (US)

(73) Assignees: Marla Deck, La Mesa, CA (US); David Deck, La Mesa, CA (US)

( * ) Notice: Subject to any disclaimer, the term of this patent is extended or adjusted under 35 U.S.C. 154(b) by 0 days.

(21) Appl. No.: 16/288,069

(22) Filed: Feb. 27, 2019

(65) Prior Publication Data

US 2019/0298645 A1    Oct. 3, 2019

Related U.S. Application Data

(60) Provisional application No. 62/641,959, filed on Mar. 12, 2018.

(51) Int. Cl.

| A61K 8/96 | (2006.01) |
| A61K 8/73 | (2006.01) |
| A61Q 1/12 | (2006.01) |
| A61K 31/19 | (2006.01) |
| A61Q 5/02 | (2006.01) |
| A61K 8/9794 | (2017.01) |

(52) U.S. Cl.
CPC .............. *A61K 8/965* (2013.01); *A61K 8/731* (2013.01); *A61K 8/9794* (2017.08); *A61K 31/19* (2013.01); *A61Q 1/12* (2013.01); *A61Q 5/02* (2013.01)

(58) Field of Classification Search
CPC ......... A61K 33/00; A61K 33/06; A61K 8/732
See application file for complete search history.

(56) References Cited

U.S. PATENT DOCUMENTS 5,605,682 A * 2/1997 Ross ...................... A61K 8/046
424/68

FOREIGN PATENT DOCUMENTS

| CN | 102559419 A | * | 7/2012 |
| CN | 104606082 A | * | 5/2015 |

OTHER PUBLICATIONS

Haslam (Journal of Archaeological Science, 2004, vol. 31, pp. 1715-1734) (Year: 2004).*
CN-104606082-A (Espacenet English translation), downloaded Mar. 2020 (Year: 2020).*
CN-102559419-A (Espacenet English translation), downloaded Mar. 2020 (Year: 2020).*
Park et al (Journal of pharmaceutical investigation, 2016, vol. 46, pp. 363-375) (Year: 2016).*

* cited by examiner

*Primary Examiner* — Mark V Stevens

(57) ABSTRACT

Sand is an irritant to people and animals. The application of the sand remover powder mixture consisting of 40% montmorillonite and 60% *Maranta arundinacea* and rubbed/wiped removes sand from effected areas of skin and hair on humans and animals better together than in their individual natural state. In some embodiments sand remover powder can contain fragrance. Sand remover powder and rubbing/wiping can be used to remove residue from hair. Sand remover powder can be used as a body powder. Some sand remover powder embodiments can be ingested.

5 Claims, 4 Drawing Sheets

Twist Cap Sift Lid;

Twist to Open, Twist to Close

SAND REMOVER FOR SKIN AND HAIR

BACKGROUND

Spending time in locations where there is sand can be an irritant to people and animals. Locations where there is sand include but not limited to beaches, lakes, rivers, sand dunes, and playgrounds. Adults, children and pets need a solution to remove sand. Talc powder and baby powders have been used in the past. Some locations provide showers to rinse sand from skin to be dried off with a sandy towel.

Sand remover powder from skin and hair invention creates a sand remover powder comprising of two powder components bentonite clay (sodium bentonite, calcium bentonite, montmorillonite) and a starch powder (*Maranta arundinacea*, arrowroot, tapioca starch, rice starch, corn starch) to remove sand. These two primary ingredients are ingestible. When scented, they may or may not be ingestible. Scents will be skin and hair safe.

Sand remover powder from skin and hair can be transported and contained in a vessel not limited to a bottle, bag, can, and or jar. Sand remover powder to be accessed and dispensed through an opening in said vessel for application to effected area of skin and hair. Dispensing opening retains a method to be resealed to reduce the intrusion of moisture.

BRIEF SUMMARY OF THE INVENTION

Sand Remover powder is a blend comprising of bentonite clay (sodium bentonite, calcium bentonite, montmorillonite) and a starch powder (*Maranta arundinacea*, arrow root, rice starch, tapioca starch, corn starch) for sand removal from skin and hair to include animal hair. Bentonite clay absorbs the moisture and the starch ingredient lifts away the sand followed by the rubbing and wiping action removes sand. Skin and/or hair are left dry and free from moisture thus reducing additional sand adhesion.

A bottle is used to contain and transport the sand remover powder invention and can be accessed through a lid for application or dispensed through a sifter cap for controlled application. (See FIG. 1, FIG. 2, FIG. 3, FIG. 4)

Adding fragrance to the powder blend comprising montmorillonite and maranta arundinacea followed by rubbing and wiping mixture removes the sand and deposits a fragrance to the skin and hair.

DETAILED DESCRIPTION

Sand remover powder consisting of montmorillonite and maranta arudinacea, applied to effected areas and rubbed briskly will remove sand better than if used in their individual natural state.

Preferred embodiment is 40% montmorillonite and 60% maranta arundinacea applied and rubbed briskly and optimal for most sand removal applications in that it absorbs moisture, does not leave behind excessive starch powder residue, and is not easily blown in the wind due to the heaviness of the clay. The combination of the thoroughly mixed powder ingredients, along with the brisk rubbing and wiping process, removes the sand better when done together than in their individual natural state.

Combine montmorillonite and maranta arundinacea in to a container. Mix, stir, agitate montmorillonite and maranta arundinacea until thoroughly blended.

To create a scented sand remover powder, combine ingredients of 39.75% montmorillonite and 59.75% maranta arudinacea and 0.5% fragrance. Add fragrance to sand remover mixture in gradual increments while machine is mixing to prevent clumping. The montmorillonite clumps if not done incrementally. Montmorillonite increases the sand remover powder density to reduce the effects of wind blowing the powder composition.

Varying the ratio of montmorillonite and maranta arundinacea along with the wiping and rubbing action allows for modifications to sand removal of different types of sand (powder, grain, tar content) and moisture content of the sand (damp, dry).

Sand remover powder consisting of two ingredients montmorillonite and maranta arundinacea, whereas the combined powder ingredients dry the skin and/or hair allowing the sand to be rubbed briskly and wiped away. These two primary ingredients are ingestible. However, when scented sand remover powder may or may not be ingestible.

Scents are skin and hair safe. Scents can be safe for ingestion depending on the type of fragrance to be added. If scented with ingestible fragrance such as essential oils the sand remover is safe for ingestion. If scented with skin and hair safe fragrance or fragrance oils then the sand remover powder is not to be considered safe for ingestion.

Figure 1:
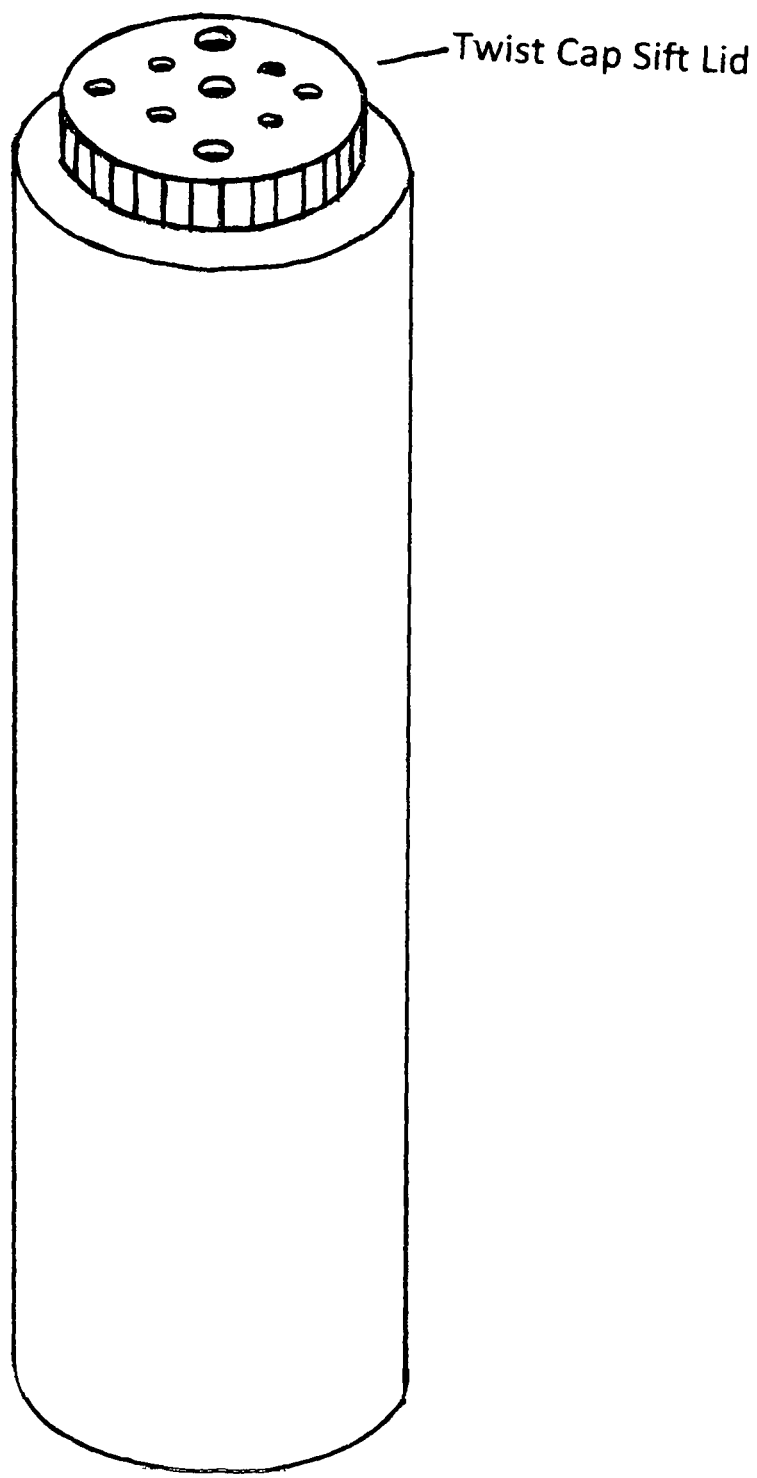
FIG. 1 shows a cylinder bottle with a twist cap for sifting powder and controlled distribution of powder product. Bottle styles, shapes, and sizes may vary.
Figure 2:
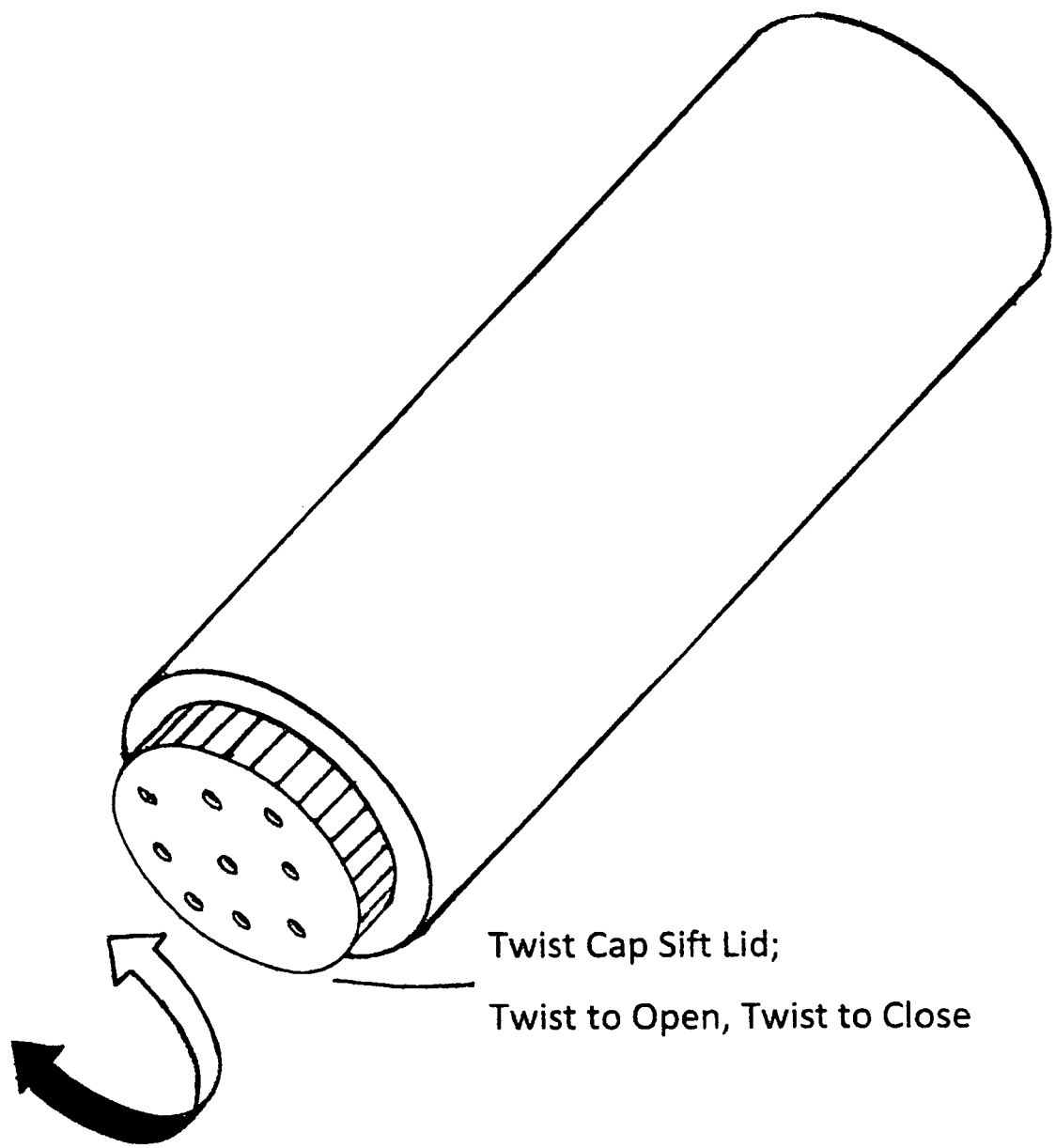
FIG. 2 illustrates sand remover powder being sifted through the holes in the cap.
Figure 3:
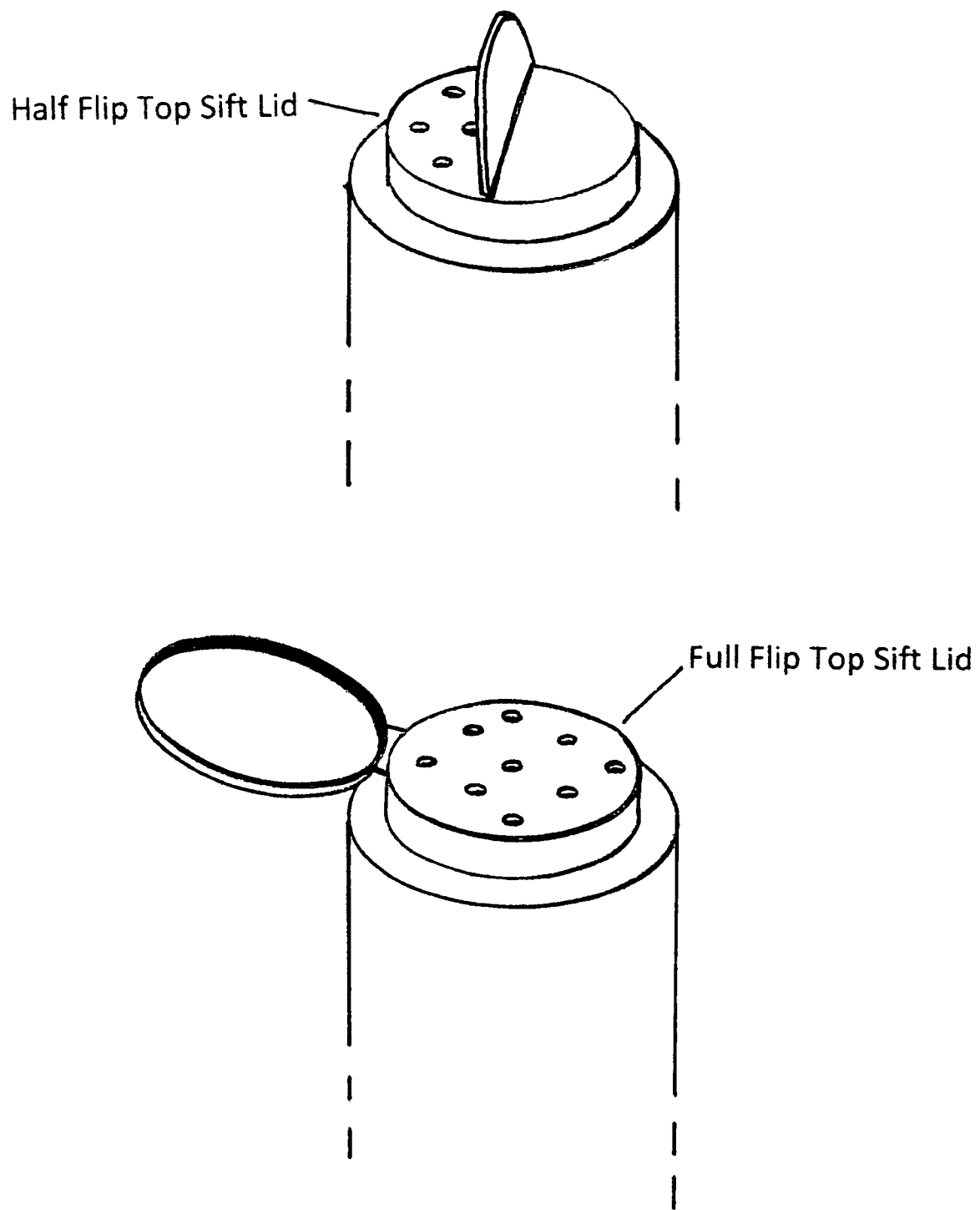
FIG. 3 presents enclosure options that will adequately contain sand remover powder lid, cap, and plug options but not limited to these styles.
Figure 4:
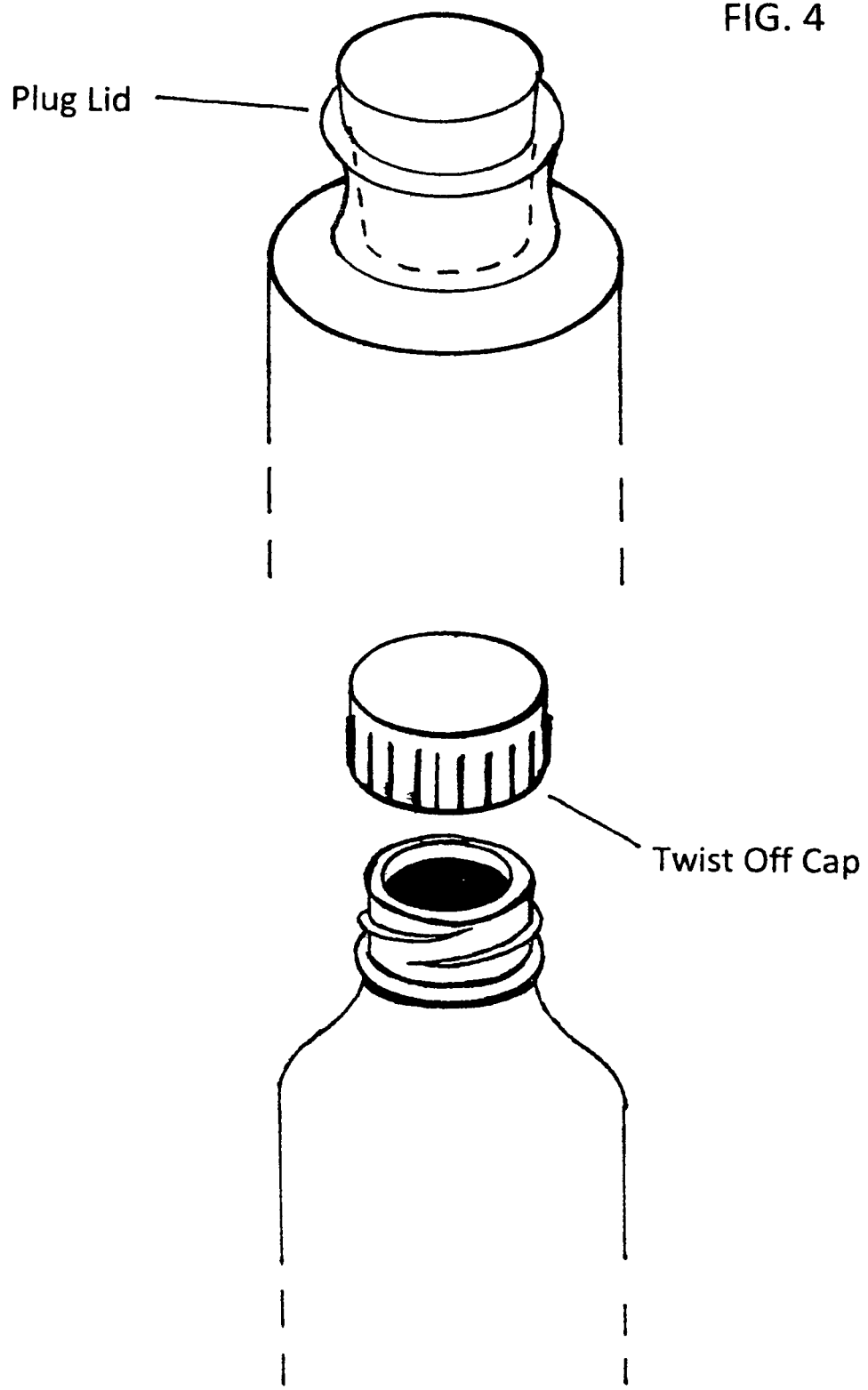
FIG. 4 presents enclosure options that will adequately contain sand remover powder lid, cap, and plug options but not limited to these styles.

Scented sand remover powder blend comprising of 39.75% montmorillonite and 59.75% maranta arundinacea with the addition of 0.5% fragrance will deposit a scent on to the skin and/or hair. Fragrance oils can be ingestible essential oils, or non-ingestible fragrance such as skin and hair safe fragrance and/or fragrance oil Sand remover powder from skin and hair can be transported and contained in a vessel not limited to a bottle, bag, can, and or jar. Sand remover powder to be accessed and dispensed through an opening in said vessel for application to effected area of skin and hair. Dispensing opening retains a method to be reseal to reduce the intrusion of moisture. The opening and closing apparatus can be a threaded cap, flip-up lid, cap, plug, twist cap with holes for dispensing the sand remover powder. (See FIG. 1, FIG. 2, FIG. 3, FIG. 4)

Directions for use of sand remover powder: sift, shake, apply sand remover powder to effected area of skin and or hair. Removal of sand with sand remover powder requires rubbing, wiping, or other form of friction to remove sand from effect area of skin and or hair. Reapply sand remover powder if desired results are not acheived. Repeat steps as Sand remover powder from skin and hair can be transported and contained in a vessel not limited to a bottle, bag, can, and or jar. Sand remover powder to be accessed and dispensed through an opening in said vessel for application to effected area of skin and hair. Dispensing opening retains a method to be resealed to reduce the intrusion of moisture. The opening and closing apparatus can be a threaded cap, flip-up lid, cap, plug, twist cap with holes for dispensing the sand remover powder. (See FIG. 1, FIG. 2, FIG. 3, FIG. 4.)

Directions for use of sand remover powder: sift, shake, apply sand remover powder to effected area of skin and or hair. Removal of sand with sand remover powder requires rubbing, wiping, or other form of friction to remove sand from effected area of skin and or hair. Reapply sand remover powder if desired results are not achieved. Repeat steps as listed as needed. Apply sand remover powder to sand on skin and wipe away sand. Apply sand remover powder to sand in hair and shake out, rub out, turn head upside down and rub powder in to scalp and hair then shake hair at the base of the hair follicle to remove sand.

Sand remover powder consisting montmorillonite and maranta arundinacea applied to effected area and wiped and rubbed briskly will remove sand better than if they were in their individual natural state. Sand remover powder can also be used as a dry shampoo to remove residue and oil buildup from scalp and hair. Scented sand remover powder blends can also be used as a dry shampoo and will deposit scent. A dry shampoo is to be understood as a means of cleaning hair and scalp from residue without the use of water. Dry shampoo may also be used on dog hair or other animal hair and use with individual discretion when using fragranced options.

Sand remover powder consisting of montmorillonite and maranta arundinacea applied to effected area and wiped and rubbed briskly will remove sand better than if they were in their individual natural state. Sand remover powder can also be used as a sand remover for animal hair.

The invention claimed is:

1. A sand remover mixture consisting of a blended powder consisting of 5%-50% of montmorillonite and 50%-95% of *Maranta arundinacea* starch, and optionally up to 3% of a fragrance, where in the sand remover mixture is capable of removing sand from hair and/or skin.

2. The sand remover mixture of claim 1, wherein the fragrance is present at a concentration of 1%-3% of the sand remover mixture.

3. A method of removing sand from the skin and/or hair of an animal or human comprising applying the sand remover mixture of claim 1 to the skin and/or hair having sand and rubbing or wiping the sand remover mixture off the skin and/or hair to remove the sand.

4. A method of removing sand or dirt from hands comprising applying the sand remover mixture of claim 1 to the hands and rubbing or wiping the sand remover mixture off the hands to remove the sand or dirt.

5. A method of removing moisture from skin and/or hair, softening skin after hair wax removal treatment, treating diaper rash, or restoring the skin comprising applying the sand remover mixture of claim 1 to the skin and/or hair.

* * * * *